(12) United States Patent
Van Bommel et al.

(10) Patent No.: US 10,240,749 B2
(45) Date of Patent: Mar. 26, 2019

(54) LIGHT SOURCE, LUMINAIRE AND SURGICAL ILLUMINATION UNIT

(71) Applicant: PHILIPS LIGHTING HOLDING B.V., Eindhoven (NL)

(72) Inventors: Ties Van Bommel, Horst (NL); Rifat Ata Mustafa Hikmet, Eindhoven (NL)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 0 days.

(21) Appl. No.: 14/764,284

(22) PCT Filed: Jan. 29, 2014

(86) PCT No.: PCT/IB2014/058628
§ 371 (c)(1),
(2) Date: Jul. 29, 2015

(87) PCT Pub. No.: WO2014/118706
PCT Pub. Date: Aug. 7, 2014

(65) Prior Publication Data
US 2015/0362151 A1    Dec. 17, 2015

Related U.S. Application Data

(60) Provisional application No. 61/757,785, filed on Jan. 29, 2013.

(51) Int. Cl.
*F21V 9/30* (2018.01)
*A61B 1/06* (2006.01)
(Continued)

(52) U.S. Cl.
CPC .............. *F21V 9/30* (2018.02); *A61B 1/0638* (2013.01); *A61B 1/0653* (2013.01); *A61B 90/30* (2016.02);
(Continued)

(58) Field of Classification Search
CPC ..... F21V 9/16; F21V 9/08; F21V 9/30; A61B 90/30; A61B 1/0638; A61B 1/0653;
(Continued)

(56) References Cited

U.S. PATENT DOCUMENTS

2002/0022273 A1* 2/2002 Empedocles ......... B01L 3/5025
436/171
2005/0099824 A1    5/2005 Dowling et al.
(Continued)

FOREIGN PATENT DOCUMENTS

JP    2005279255 A    10/2005
JP    2008258356 A    10/2008
(Continued)

*Primary Examiner* — Anh T Mai
*Assistant Examiner* — Glenn D Zimmerman (57) ABSTRACT

The Invention provides a light source, a luminaire and a surgical illumination unit in which two narrow-band light emitters both emit light in a narrow spectral peak having a full-width-half-maximum equal to or smaller than 40 nanometers. Both of the narrow-band light emitters have a different central emission wavelength within a blue color-range, within a green color range or within a red color-range. At least one of the two narrow-band light emitters comprises a luminescent material for generating the narrow spectral peak. The light source is further configured such that a distance between the narrow spectral peaks of the two narrow-band light emitters prevents overlap of the narrow spectral peaks. Due to the individual narrow spectral peaks, a color contrast within one of the color-ranges is significantly enhanced.

13 Claims, 5 Drawing Sheets

(51) Int. Cl.
*F21V 9/08* (2018.01)
*A61B 90/30* (2016.01)
*F21W 131/20* (2006.01)
*A61B 5/00* (2006.01)
*F21W 131/205* (2006.01)
*F21Y 115/10* (2016.01)

(52) U.S. Cl.
CPC .............. *F21V 9/08* (2013.01); *A61B 5/0075* (2013.01); *A61B 2090/304* (2016.02); *A61B 2090/309* (2016.02); *F21W 2131/20* (2013.01); *F21W 2131/205* (2013.01); *F21Y 2115/10* (2016.08)

(58) Field of Classification Search
CPC ........ A61B 2090/304; A61B 2090/309; A61B 5/0075; F21W 2131/20; F21W 2131/205; F21Y 2101/00; F21Y 2115/10
USPC ......... 362/231, 260, 800, 227; 313/504, 512
See application file for complete search history.

(56) References Cited

U.S. PATENT DOCUMENTS

| | | | |
|---|---|---|---|
| 2007/0219605 A1* | 9/2007 | Yaroslavsky | A61N 5/0613 607/100 |
| 2007/0241657 A1 | 10/2007 | Radkov et al. | |
| 2008/0183081 A1* | 7/2008 | Lys | A61N 5/0616 600/477 |
| 2008/0246017 A1* | 10/2008 | Gillies | B82Y 20/00 257/13 |
| 2008/0296555 A1* | 12/2008 | Miller | C09K 11/025 257/14 |
| 2010/0123155 A1 | 5/2010 | Pickett et al. | |
| 2010/0140551 A1 | 6/2010 | Parce et al. | |
| 2010/0254115 A1* | 10/2010 | Wegh | F21S 10/02 362/84 |
| 2011/0037840 A1* | 2/2011 | Hiltl | A61B 90/30 348/61 |
| 2011/0176291 A1 | 7/2011 | Sanders et al. | |
| 2011/0285962 A1* | 11/2011 | Ellinger | G02B 27/2207 353/7 |
| 2011/0292660 A1* | 12/2011 | Eichelberger | G02B 6/0006 362/311.02 |
| 2012/0068118 A1 | 3/2012 | Parce et al. | |
| 2012/0113672 A1 | 5/2012 | Dubrow et al. | |

FOREIGN PATENT DOCUMENTS

| | | | | |
|---|---|---|---|---|
| JP | 2010162214 A | 7/2010 | | |
| JP | 2010287323 A | 12/2010 | | |
| WO | WO 2014068440 A1 * | 5/2014 | ........... | H01L 33/504 |

* cited by examiner

LIGHT SOURCE, LUMINAIRE AND SURGICAL ILLUMINATION UNIT

CROSS-REFERENCE TO PRIOR APPLICATIONS

This application is the U.S. National Phase application under 35 U.S.C. § 371 of International Application No. PCT/IB14/058628, filed on Jan. 29, 2014, which claims the benefit of U.S. Provisional Patent Application No. 61/757,785, filed on Jan. 29, 2013. These applications are hereby incorporated by reference herein.

FIELD OF THE INVENTION

The invention relates to light source comprising at least two narrow-band emitters, each emitting light in a narrow spectral peak. The invention further relates to a luminaire and to a surgical illumination unit.

BACKGROUND OF THE INVENTION

Such light sources are known per se. They are used, inter alia, in luminaires for general lighting purposes, for example, for office lights, for shop lights or, for example, for shop window lights. These light sources are also used, inter alia, in special lighting applications such as hospital operating illumination units, for example, used during surgery, or special lighting applications used, for example, in graphical industry, printing industry, or specific shop light applications and advertisements.

A current trend in light sources is to improve the efficiency of the light source, for example, by using semiconductor devices as light emitting devices. These semiconductor light emitting devices are, for example, Light Emitting Diodes (further also indicated as LED) or semiconductor LASERs. Recently also Organic LEDs (also further indicated as OLED) are often used. These semiconductor light emitting devices typically emit light within a limited spectral bandwidth at relatively high intensity. To ensure that these light sources comprising semiconductor light emitting devices still have decent color rendering, often luminescent materials are included in the light source. In a luminescent material, light of a first spectral distribution is absorbed and is partially converted into light of a second spectral distribution. Typically the absorbed photons are emitted as photons having a lower frequency (or longer wavelength: Stokes shift) and the loss of energy per photon is transformed into heat. Alternatively, the emitted photons may have higher frequency (or shorter wavelength: anti-Stoke shift).

One example of such light source comprising a luminescent material can be found in the published patent application US2010/0123155A1 which relates to a semiconductor nanoparticle-based light-emitting device. This device comprises a LED that is arranged to emit blue primary light upon the application of current and which is submerged in a commercially available LED encapsulant in which is embedded a plurality of quantum dot-containing polymeric beads. Although the known light sources usually have a relatively good color rendering, often contrast between colors is not good enough.

SUMMARY OF THE INVENTION

It is an object of the invention to provide a light source having improved color contrast.

A first aspect of the invention provides a light source. A second aspect of the invention provides a luminaire. A third aspect of the invention provides a surgical light source. Advantageous embodiments are defined in the dependent claims.

A light source in accordance with the first aspect of the invention comprises two narrow-band light emitters both emitting light in a narrow spectral peak having a full-width-half-maximum equal to or smaller than 40 nanometers. Each of the two narrow-band light emitters comprises a different central emission wavelength within a blue color-range or within a green color-range or within a red color-range. At least one of the two narrow-band light emitters comprises a luminescent material for generating the narrow spectral peak, and a distance between the narrow spectral peaks of the at least two narrow-band light emitters is configured to prevent overlap of the narrow spectral peaks. The light source according to the invention generates in at least one of the blue, green or red color-ranges of the visible light spectrum a plurality of narrow spectral peaks in which at least one of the two narrow spectral peaks is generated using a luminescent material. One of the two narrow-band light emitters may, for example, be tuned to a predefined wavelength to enhance a contrast of the predefined wavelength, while the separation of the emitted narrow spectral peaks strengthens the contrast perceived. This strongly increased contrast may, for example, be used in surgery. In such an embodiment the surgical instruments may, for example, have a predefined blue color which is enhanced by at least one of the narrow-band light emitters emitting light in the blue color-range. In such an embodiment, the light from the light source tuned to the same color as the surgical instruments significantly enhance the visibility of the surgical instruments for the people performing the surgery. In an alternative embodiment of the light source, the light source may be used for advertisement purposes or in the graphical industry to strongly enhance optical emphasis of a specific product that is advertised. In such an embodiment, one of the two narrow-band light emitters may, for example be tuned to a color present in a logo of a company or brand name. Using the light source according to the invention, for example, in a shop will enhance the contrast of the specific logo or brand name compared to other brands or logos present in the shop, and as such enhances the visibility of that specific logo or brand. Even further alternatively, the increased contrast may be used in visual systems for robots in which, for example, information for the robot is visually hidden in a colorful image also comprising the predefined wavelength. The visibility of the hidden information will be enhanced when using the light source according to the invention for example mounted on the robot. In such an embodiment, the robot may further comprise a specific camera tuned to the predefined wavelength, such that the hidden information of which the contrast is enhanced, will be even further enhanced by using the specific camera.

In the light source according to the invention a narrow-band light emitter is used. Such narrow-band light emitter emits substantially all light in a single emission peak or has a significantly enhanced narrow-band emission peak in its light emission spectrum (a maximum intensity in the narrow-band emission peak at least ten fold the maximum intensity in the remainder of the emission spectrum). Examples of such narrow-band light emitters are LEDs, semiconductor Lasers or OLEDs. Other examples of such narrow-band light emitters are some luminescent materials such as quantum dot materials (also known as nano-crystal materials) and rare-earth metal complexes such as e.g.

Europium, Cerium. A central emission wavelength is a wavelength in the spectral distribution of the narrow spectral peak which corresponds to the wavelength at the center of the full width at half maximum of the narrow spectral peak. For narrow-band light emitters this central emission wavelength often corresponds to the wavelength at maximum emission intensity. The light source according to the invention are configured such that the at least two narrow spectral peaks in the light source do not overlap. This is achieved when the distance between the two neighboring spectral light peaks at half maximum intensity of the highest spectral light peak has a distance equal or larger than the Full-Width-Half-Maximum value. If the two neighboring spectral light peaks have different FWHM values, the distance between the two neighboring spectral light peaks should be equal to or larger than an average of the two FWHM values. The light source according to the invention may, of course, have additional substantially identical narrow-band light emitters to, for example, increase the overall intensity of the light source, for example, at the narrow spectral peaks. For these substantially identical narrow-band light emitters there might be some minor emission variations which may be caused by, for example, manufacturing variations.

In the light source according to the invention the central emission wavelength of the at least two narrow spectral peaks lie within the blue color-range or the green color-range or the red color-range. The blue color-range is defined between 380 nanometer and 495 nanometer, the green color-range is defined between 495 nanometer and 590 nanometer, and the red color-range is defined between 590 nanometer and 800 nanometer.

In an embodiment of the light source according to the invention, the central emission wavelength of the two narrow spectral peaks lie within a wavelength range between 590 nanometers and 800 nanometers. Also this embodiment of the invention may be beneficial in surgery in which, for example, one of the two narrow spectral peaks is tuned to the specific color of specific tissue which need to be operated upon. The use of the light source according to the invention enables to significantly enhance the contrast between the specific tissue and its surroundings which may even result in sufficient contrast enhancement such that no contrast fluids may be required during surgery.

The luminescent material may comprise any one of the materials from a list comprising quantum dots, quantum rods, quantum tetrapods, nano-crystals, and rare earth metal complexes with narrow emission characteristics. The use of these materials is to ensure that the central wavelength of the light emitted may be tuned relatively accurately. Using quantum dots, quantum rods, quantum tetrapods or nano-crystals, this tuning might be relatively simple, for example, via a change in dimension of the quantum dot. Quantum dots (quantum rods and quantum tetrapods) or nano-crystals are small crystals of semiconducting material which generally have a width or diameter of only a few nanometers. The luminescent material crystals comprise particles showing quantum confinement and have at least in one dimension a size in the nanometer range. When excited by incident light, a quantum dot crystal emits light of a color determined by the size and the material of the crystal. Light of a particular color can therefore be produced by adapting the size of the quantum dots. Most known quantum dots with an emission in the visible range are based on cadmium selenide (CdSe) having a shell of cadmium sulfide (CdS) and/or zinc sulfide (ZnS). Cadmium free quantum dots such as indium phosphode (InP), and copper indium sulfide (CuInS2) and/or silver indium sulfide (AgInS2) may also be used. Quantum dots show very narrow emission band and thus they show saturated colors. Cadmium-containing quantum dot emitter may emit light having a narrow spectral peak up to 15 or 20 nanometers (FWHM). Cadmium-free quantum dots may emit light having a narrow spectral peak up to 25 or 30 nanometers (FWHM). An example of a rare earth metal complex being a narrow-band light emitting luminescent material is, for example, a lanthanide complex such as $Eu_2(dbt)_3\text{-}4H_2O$ which has a narrow spectral peak of approximately 5 nanometer (FWHM).

Optionally, the central emission wavelength of the narrow spectral peak of the light emitted by the at least one narrow-band light emitter comprising the luminescent material is tuned to a predefined wavelength for enhancing a contrast of a predefined visible element. Especially when using quantum dots or nano-crystals, the central emission wavelength of the narrow spectral peak may relatively easily be tuned, for example, by changing a dimension of the quantum dot or nano-crystals used in the light source. As indicated before, quantum dots are small crystals of semiconductor materials. They are typically produced in a liquid in which the crystals are grown to a specific size—this size determines the central emission wavelength of the quantum dot. So it is relatively easy to tune the central emission wavelength of the luminescent material to the predefined wavelength by, for example, changing the growing conditions such as time, temperature and crystal concentrations in the fluid. Using such tuned luminescent material in a light source according to the invention may be used to enhance the color in a brand or logo or the enhance the color of a specific type of tissue during surgery.

In an embodiment of the light source according to the invention, the blue color-range or green color-range or red color-range is expanded to an expanded wavelength range between 400 nanometer and 800 nanometer, and wherein the light source is configured to comprise at least 5 narrow-band light emitters each emitting light in a narrow spectral peak having a full-width-half-maximum equal to or smaller than 40 nanometers and each having a different central emission wavelength within the expanded wavelength range. The central wavelength of the at least 5 narrow-band light emitters may, for example, be substantially evenly distributed over the expanded wavelength range such that the light source is able to render 5 different colors relatively good, while the separation between the individual narrow spectral peaks enhance the color contrast between the individual colors across the whole visible range. Also this substantially equally distribution may, for example, be locally fine-tuned to a specific color which requires enhancement, for example, for advertisement purposes or medical purposes. In advertisement, a plurality of narrow-band light emitters in the light source may all be tuned to different colors in a brand or logo, such that the visibility of the whole brand or logo is strongly enhanced when using the light source according to the invention. Alternatively, in the two previous medical examples, a single light source according to the invention may have a narrow-band light emitter specifically tuned to a specific tissue-type which need to be operated upon, while a different narrow-band light emitter in the same light source is tuned to a color corresponding to the color of the surgical instruments used such that both are enhanced at the same time using a single light source according to the invention.

Optionally, a distance between the narrow spectral peaks at half-maximum intensity of the narrow spectral peak is arranged to be equal to or larger than 40 nanometers. This distance is not a distance between the central wavelengths of two neighboring narrow spectral peaks, but is a spacing between two neighboring peaks and ensures sufficient distance between the two narrow spectral peaks to maintain significant contrast between the two neighboring peaks.

Optionally, a sum of the full-width-half-maximum value of the narrow spectral peaks within the expanded wavelength range is substantially equal to half the expanded wavelength range. A benefit of such spread of the narrow spectral peaks is that the expanded wavelength range is substantially completely filled with individual narrow spectral peaks of the plurality of narrow-band light emitters to ensure color rendering across the complete expanded wavelength range, while ensuring good contrast between individual colors.

Optionally, an overall light emission spectrum within the blue color-range, green color-range, red color-range, or within the expanded wavelength range further comprises light emitted in a wide spectral band having an intensity equal to or less than 25% of an average intensity of the plurality of narrow spectral peaks (the power in this background illumination is significantly less than the power in the narrow spectral peaks). The wide spectral band is significantly larger than 40 nm and may contain some substantially continuous light emission spectrum as a kind of back-ground emission spectrum. A benefit of this embodiment is that the low intensity wide spectral band enhances the minimum color rendering characteristics of the light source within the predefined wavelength range or the expanded wavelength range while maintaining the strong contrast enhancement between individual colors. Also in this embodiment, the central emission wavelength of some of the narrow-band light emitters may be tuned to a specific color which requires enhancement.

In an embodiment of the light source, the luminescent material may be arranged on a light exit surface of the light emitting device, and/or in a vicinity of the light exit surface of the light emitting device, and/or in a remote location from the light exit surface of the light emitting device.

Optionally, the luminescent material comprises a mixture of different luminescent materials, at least one of the different luminescent materials being a narrow-band light emitter emitting light at a different central wavelength and having a narrow spectral peak having a full-width-half-maximum equal to or smaller than 40 nanometers. The other luminescent materials in the mixture may be in a different color range or may have an intensity significantly lower than the intensity of the narrow-band light emitting luminescent materials such that they function as a kind of background illumination. Alternatively more than one of the different luminescent materials are narrow-band light emitters.

Optionally, the light emission spectrum of the light source comprises light emitted by the light emitting device. Often blue LEDs are used for illuminating the luminescent material. Because the blue LED also may function as a narrow-band light emitter, the light source may be configured such that only part of the blue light emitted by the LED is absorbed by the luminescent material and the remainder of the blue light contributes to the overall emission spectrum of the light source.

The luminaire according to the second aspect comprises the light source according to the invention.

The surgical light source according to the third aspect comprises the light source according to the invention.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful.

Modifications and variations of the color conversion arrangement, the lighting unit and the solid state light emitter package, which correspond to the described modifications and variations of the color conversion arrangement, can be carried out by a person skilled in the art on the basis of the present description.

BRIEF DESCRIPTION OF THE DRAWINGS

In the drawings:

FIG. 3b shows the absorption and emission spectra of this rare earth complex, FIGS. 4a to 4d schematically further show different positioning of the luminescent material with respect to the light emitters, and FIGS. 5a to 5d schematically shows embodiment of a light source, a luminaire and a surgical illumination unit, respectively.

It should be noted that items denoted by the same reference numerals in different Figures have the same structural features and the same functions, or are the same signals. Where the function and/or structure of such an item have been explained, there is no necessity for repeated explanation thereof in the detailed description.

The Figures are purely diagrammatic and not drawn to scale. Particularly for clarity, some dimensions are exaggerated strongly.

DETAILED DESCRIPTION

Figure 1A:
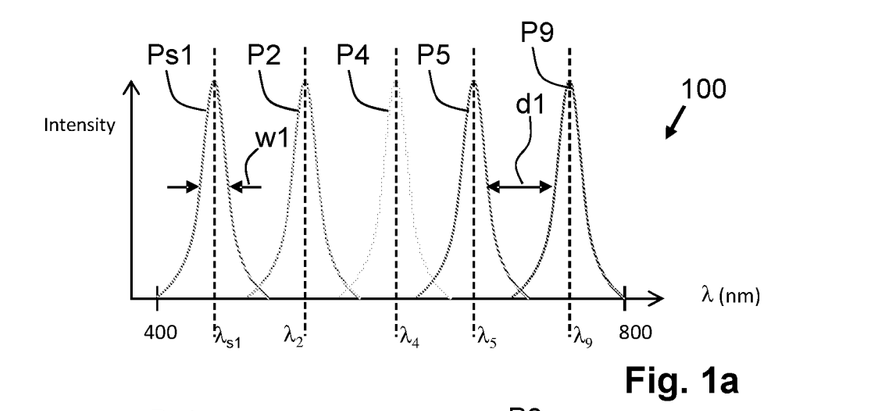
FIGS. 1a to 1c show different emission spectra of light sources according to the invention, FIGS. 2a to 2c schematically show different configurations of a light source according to the invention comprising a plurality of light emitting devices to generate the plurality of narrow-band light emitters.
Figures 1B, 1C:
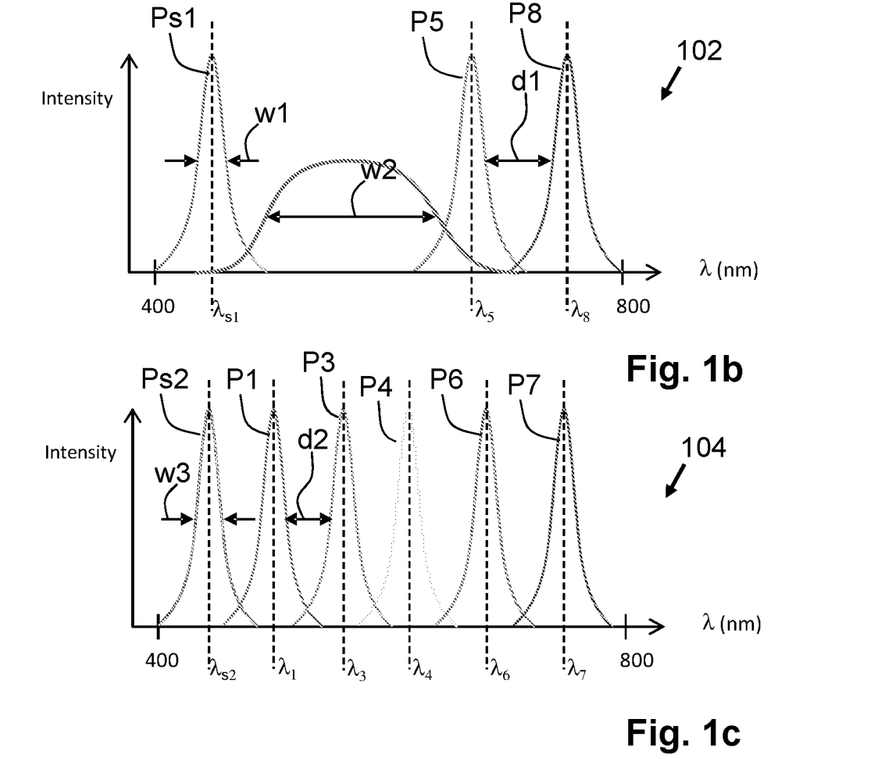

FIGS. 1a to 1c show different emission spectra 100, 102, 104 of a light source 500, 510 (see FIGS. 2 and 5) according to the invention. The light source 500, 510 according to the invention comprises a plurality of narrow-band light emitters 210, 220-228 (see FIG. 2). Such narrow-band light emitters 210, 220-228 comprise, for example, a light emitting device 210 emitting light in narrow spectral peak Ps1, Ps2, for example, solid state light emitters such as Light Emitting Diodes, Organic Light Emitting Diodes or Laser diodes; or the narrow-band light emitters 210, 220-228 comprise luminescent light conversion elements 220-228 which comprise luminescent materials emitting light in a narrow spectral peak P1-P9. A width w1, w3 of these narrow spectral peaks P1-P9 of the narrow-band light emitters 210, 220-228 is equal to or less than 40 nanometers and a distance d1, d2 between two neighboring spectral emission peaks P1-P9 is such that the two neighboring spectral emission peaks P1-P9 substantially do not overlap. A benefit of the light source 500, 510 is that this emission spectrum 100, 102, 104 enables a high color contrast and enables to fine-tune the emission spectrum 100, 102, 104 such that the color contrast occurs between predefined visible elements. Especially when using at least two narrow-band light emitters 210, 220-228 having a different central emission wavelength λ1-λ9, λs1, λs2 within a blue color-range or within a green color-range or within a red color-range, the color contrast within that specific color range can be significantly enhanced. The light source 500, 510 according to the invention may further comprise a light emitter 230 which emits light in a wider spectral range w2. This additional light emitter 230 may be used to enhance the overall color rendering in at least a part of the visible spectrum while maintaining good color contrast.

Luminescent materials emitting light in a narrow spectral peak P1-P9 often show some kind of quantum confinement. Such luminescent material often comprises particles showing quantum confinement and having at least in one dimension a size in the nanometer range are, for example, quantum dots, quantum rods or quantum tetrapods. Having a size in one dimension in the nanometer range means that, for example, if the particles are substantially spherical, their diameter is in the nanometer range. Or, this means, for example, if they are wire-shaped, that a size of a cross-section of the wire is in one direction in the nanometer range. A size in the nanometer range means that their size is at least smaller than 1 micrometer, thus, smaller than 500, 510 nanometers, and larger or equal to 0.5 nanometer. In an embodiment, the size in one dimension is smaller than 50 nanometers. In another embodiment the size in one dimension is in the range from 2 to 30 nanometers. Quantum dots are small crystals of semiconducting material generally having a width or diameter of only a few nanometers. When excited by incident light, a quantum dot emits light of a color determined by the size and material of the crystal. Light of a particular color can, therefore, be produced by adapting the size of the dots. Most known quantum dots with emission in the visible range are based on cadmium selenide (CdSe) with a shell such as cadmium sulfide (CdS) and zinc sulfide (ZnS). Cadmium free quantum dots such as indium phosphide (InP), and copper indium sulfide ($CuInS_2$) and/or silver indium sulfide ($AgInS_2$) may also be used. Quantum dots show very narrow emission band and thus they show saturated colors. Furthermore, the emission color can easily be tuned by adapting the size of the quantum dots. Any type of quantum dot known in the art may be used in the present invention, provided that it has the appropriate wavelength conversion characteristics.

Alternative luminescent materials also emitting light in a narrow spectral peak are some rare earth metal complexes, such as Europium and Cerium. One example of such rare earth metal complex is shown in FIG. 3.

For a first embodiment of the light source 500, 510, the light emission spectrum 100 is shown in FIG. 1*a*. The light source 500, 510 according to the invention comprises, for example, a plurality of narrow-band light emitters 210, 220-226 (see FIG. 2) emitting light in narrow spectral peaks Ps1, P2, P4, P5, P9 distributed across the whole visible light spectrum. A width w1 of these narrow spectral peaks Ps1, P2, P4, P5, P9 is equal to or less than 40 nanometers and a distance d1 between two neighboring spectral emission peaks P5, P9 is such that the two neighboring spectral emission peaks Ps1, P2, P4, P5, P9 substantially do not overlap. In the emission spectrum 100 as shown in FIG. 1*a*, substantially the whole emission spectrum 100 is constituted of individual narrow spectral peaks Ps1, P2, P4, P5, P9 distributed across the whole visible spectrum. In the schematic spectrum shown 100 shown in FIG. 1*a* all narrow spectral peaks Ps1, P2, P4, P5, P9 substantially have the same intensity—however it will be clear to a person skilled in the art that the intensities may vary without departing from the scope of the invention. A benefit of a light source 500, 510 having such an emission spectrum 100 is that the color contrast when using such light source 500, 510 is very high while still emitting substantially white light. In an embodiment of this light source 500, 510, some or all of the individual narrow spectral peaks Ps1, P2, P4, P5, P9 may be tuned to a specific central emission wavelength λs1, λ2, λ4, λ5, λ9, for example, corresponding to colors which are present in a brand or logo of a company. Using the light source 500, 510 comprising the emission spectrum 100 results in a strong contrast enhancement of the brand or logo having substantially matching colors, especially when compared to brands or logos that do not have matching colors. Such light source 500, 510 may, for example, be used in shop lighting to enhance the visibility of specific brands compared to other brands.

Figure 2A:
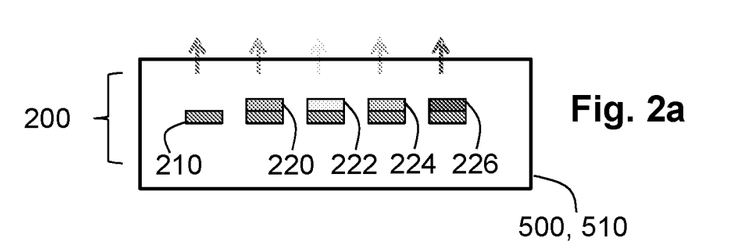

The light source 500, 510 having the emission spectrum shown in FIG. 1*a* may have been generated using an arrangement 200 of narrow-band light emitters 210, 222-226 inside the light source 500, 510 as shown in FIG. 2*a*. The configuration of FIG. 2*a* shows a light emitting device 210 which emits a narrow spectral peak Ps1 in the blue color-range, which is used as output of the light source 500, 510. The configuration shown in FIG. 2*a* comprises four more light emitting devices 210 of which the light is converted using light conversion elements 220, 222, 224, 226 being the narrow-band light emitters 220-226 comprising luminescent material and emitting light in the narrow spectral peaks P2, P4, P5, P9. Two of these light conversion elements 220, 222 emit light having a central emission wavelength λ2, λ4 in the green color-range and two of these light conversion elements 224, 226 have a central emission wavelength λ5, λ9 in the red color-range.

The emission spectrum 102 shown in FIG. 1*b* comprises a combination of narrow spectral peaks Ps1, P5, P8 from narrow-band light emitters 210, 224, 226 (see FIG. 2) together with a light emitter 230 (see FIG. 2) which emits light in a wider spectral range w2. This additional light emitter 230 has a central emission wavelength λb in the green color-range of the emission spectrum 102 of the light source 500, 510 and may be used to enhance the overall color rendering in green color-range of the emission spectrum 102. Also in the schematic spectrum 102 shown in FIG. 1*b* all narrow spectral peaks Ps1, P5, P6 substantially have the same intensity—however, as indicated before, it will be clear to a person skilled in the art that the intensities may vary without departing from the scope of the invention. A light source 500, 510 having the emission spectrum 102 shown in FIG. 1*b* may, for example, be used as light source 500, 510 in a surgical illumination unit 504 (see FIG. 5). In such an embodiment, at least one of the central emission wavelengths λ5, λ9 of the narrow spectral peaks P5, P8 in the red color-range may be tuned to the color of a specific tissue (not shown) which needs to be operated upon, while, for example, the narrow spectral peak Ps1 in the blue color-range may be tuned to a central emission wavelength λs1 color of the instruments used during surgery (not shown) while the light emitter 230 emitting the wider spectral range w2 in the green color-range is used to maintaining overall good color contrast and visibility.

Figure 2B:
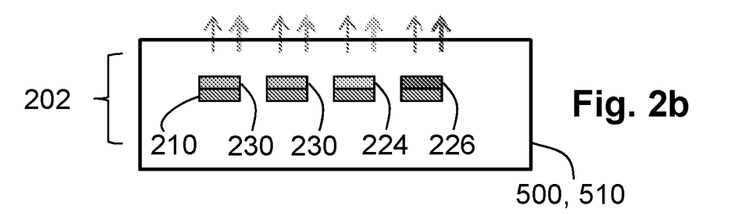

The light source 500, 510 having the emission spectrum shown in FIG. 1*b* may have been generated using an arrangement of narrow-band light emitters 210, 220-228 inside the light source 500, 510 as shown in FIG. 2*b*. The configuration of FIG. 2*b* shows a light emitting device 210 which emits a narrow spectral peak Ps1 in the blue color-range, which is partially used as output of the light source 500, 510. The configuration shown in FIG. 2*b* comprises light conversion elements 224, 226, 230 comprising luminescent material for partially converting light of the light emitting device 210 into light of a longer wavelength. Two of these light conversion elements 224, 226 being narrow-band light emitters 224, 226 emitting light in a narrow spectral peak P5, P8 having a central emission wavelength λ5, λ8 within the red color-range. Other luminescent conversion elements 230 comprise a luminescent material or a mixture of luminescent materials which convert part of the light of the light emitting device 210 into light having the wider spectral range w2 in the green color-range.

The emission spectrum 103 shown in FIG. 1c comprises an emission spectrum of a light source 500, 510 according to the invention in which the light source 500, 510 comprises a plurality of narrow-band light emitters 210, 220-228 emitting a plurality of narrow spectral peaks Ps2, P1, P3, P4, P6, P7 having a central emission wavelength λs2, λ1, λ3, λ4, λ6, λ7 distributed across the visible spectral range. Again the schematic spectrum 103 in FIG. 1c shows all narrow spectral peaks Ps1, P5, P6 substantially at the same intensity however, it will be clear that the intensities may vary without departing from the scope of the invention. The emission spectrum 103 is similar to the spectrum shown in FIG. 1a, only now one additional narrow-band light emitter is included to generate an emission spectrum having 6 narrow spectral peaks Ps2, P1, P3, P4, P6, P7.

Figure 2C:
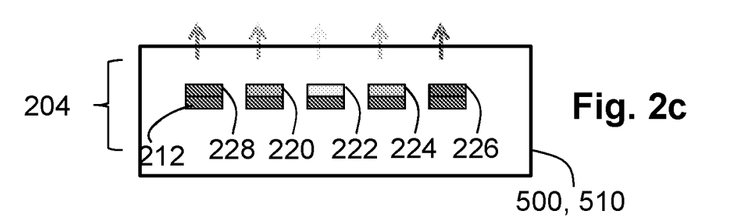

FIGS. 2a to 2c schematically show different configurations of a light source 500, 510 according to the invention comprising a plurality of light emitting devices 210, 212 to generate the plurality of narrow-band light emitters 210, 220-228. The embodiments shown in FIGS. 2a and 2b have already been described herein above. The embodiment shown in FIG. 2c comprises a light emitting device 212 which, for example, emits ultraviolet light. This ultraviolet light is converted by the light conversion elements 220-228 being the narrow-band light emitters 220-228 into visible light. When choosing luminescent materials that emit light in the different narrow spectral peaks Ps1, P2, P4, P5, P9 similar to the narrow spectral peaks Ps1, P2, P4, P5, P9 shown in FIG. 1a, the configuration of FIG. 2c may also be used to generate the emission spectrum 100 shown in FIG. 1a.

Figure 3A:
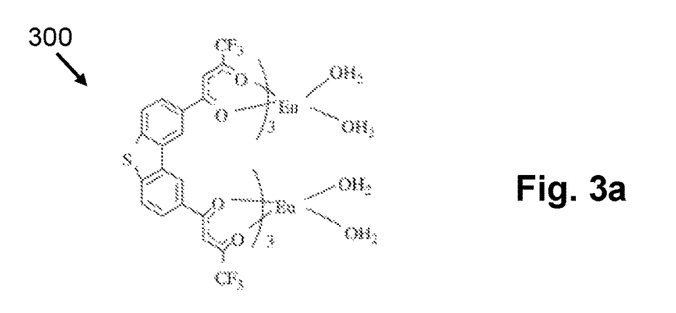
FIG. 3a shows a structural diagram of a rare earth metal complex comprising Europium.
Figure 3B:
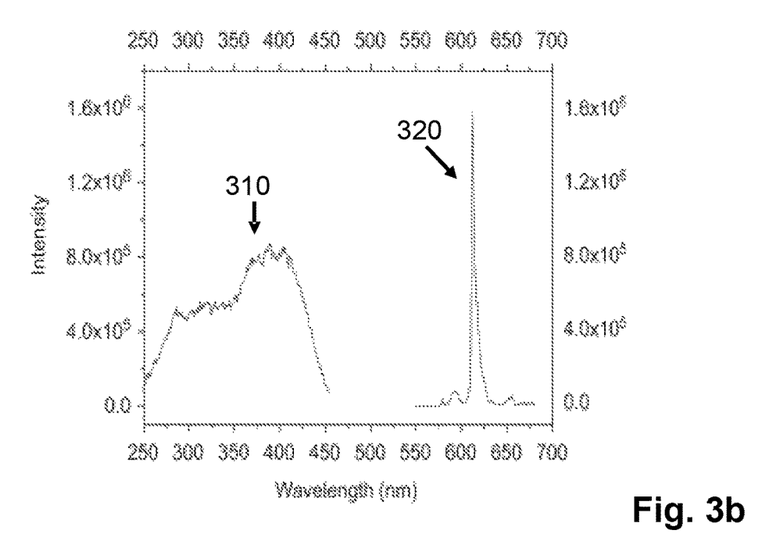

FIG. 3a shows a structural diagram 300 of a rare earth metal complex comprising Europium, and FIG. 3b shows the absorption 310 and emission spectrum 320 of this rare earth complex. As can be seen in the emission spectrum 320 of this rare earth metal complex, some residual emission intensity may be around the narrow spectral emission peak without departing from the scope of the invention.

FIGS. 4a to 4d schematically further show different positioning of the light conversion elements 410-416 comprising the luminescent material with respect to the light emitting device 210. In the embodiment shown in FIG. 4a the light conversion element 410 is applied in direct contact with the light emitting device 210. In such an embodiment, the light emitting device 210 comprises a light exit window (not indicated) being a window or opening from which the light is emitted from the light emitting device 210. The light conversion element 410 may be a substance directly applied on the light exit window or may be a separate element which is applied to the light exit window. A benefit of this embodiment is that combination of light emitting device 210 and the light conversion element 410 is relatively compact.

Figure 4A:
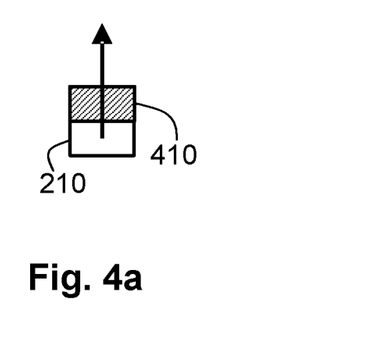
Figure 4B:
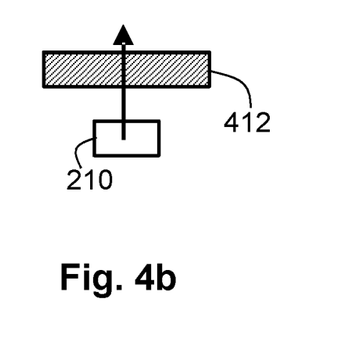

In the embodiment shown in FIG. 4b the light conversion element 412 is arranged in the vicinity of the light emitting device 210. A benefit of this embodiment is that the temperature of the luminescent material in the light conversion element 412 is lower compared to the embodiment shown in FIG. 4a which improves the life-time of the luminescent material.

Figure 4C:
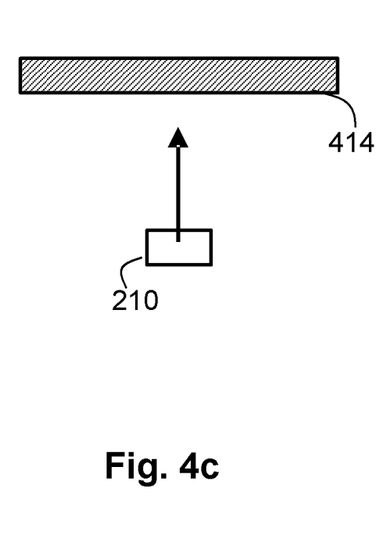
Figure 4D:
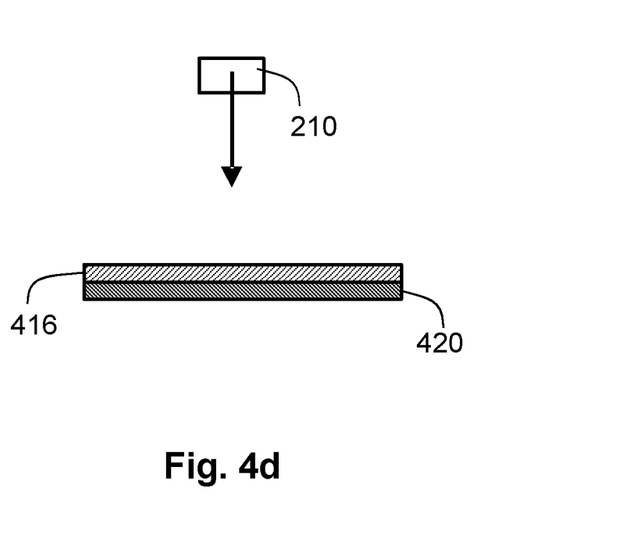
Figure 5A:
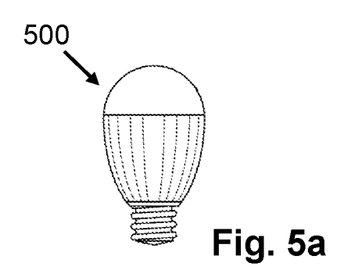
Figure 5B:
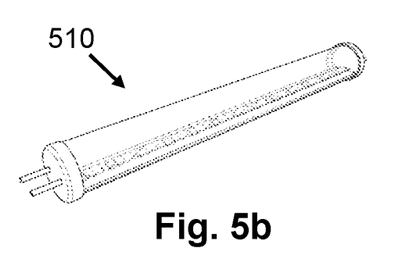
Figure 5C:
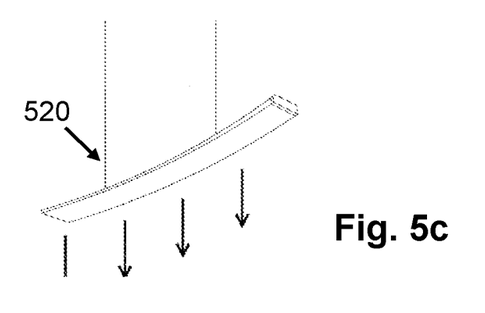
Figure 5D:
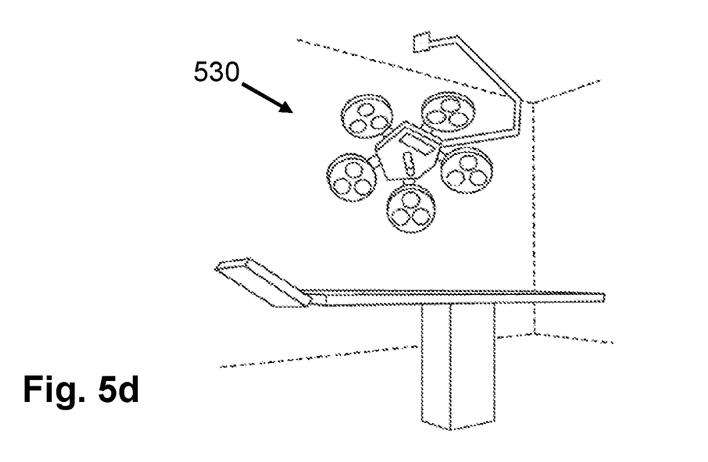

The embodiments shown in FIGS. 4c and 4d show the light conversion element 414, 416 even more remote from the light emitting device 210. Such arrangement of the light conversion element 414, 416 is also known as a "remote phosphor arrangement". Now, the light conversion element 414, 416 is located at such a distance from the light emitting device 210 that the temperature of the light conversion element 414, 416 is very much lower compared to the temperature of the light emitting device 210, further improving the life-time of the luminescent material. Typically, luminescent material degrade when exposed to relatively high temperature. Different luminescent materials may withstand different temperature ranges, and so each of the above mentioned arrangement may be chosen depending on the luminescent material chosen in the light conversion element 414, 416. In the embodiment shown in FIG. 4d, the light conversion element 416 is arranged on a reflecting surface 420. Light emitted by the light emitting device 210 passes through the light conversion element 416 twice. As such, the light conversion element 416 in FIG. 4d only needs to have half of the thickness of the light conversion element 414 shown in FIG. 4c to achieve the similar conversion efficiency.

FIGS. 5a to 5d schematically shows an embodiment of a light source 500, a light source 510, a luminaire 520, and a surgical illumination unit 530, respectively. The light source 500, 510 shown in FIGS. 5a and 5b may comprise, for example, any of the arrangements shown in FIGS. 2a to 2c or may comprise different arrangements according to the invention. The form-factor of the light source 500 shown in FIG. 5a may be useable in conventional incandescent lighting housings and the form-factor of the light source 510 shown in FIG. 5b may be useable in a conventional tubular lighting housing. The luminaire 520 shown in FIG. 5c and the surgical illumination unit 530 according to the invention may comprise any of the light sources 500, 510 according to the invention.

The light source, lamp or luminaire preferably produces white light. Preferably light which has a correlated color temperature (CCT) along the black body line (BBL). More preferably, the light source has a color rendering index (CRI) of at least 80.

Phosphors which can be used for background illumination includes but are not limited to inorganic phosphors, organic phosphors or combinations of quantum dots (i.e. different materials/sizes).

The inorganic luminescent material may comprises a yellow or yellow/green emitting inorganic phosphor, such as YAG and/or LuAG, or a red inorganic phosphor such as ECAS and/or BSSN.

Examples of inorganic phosphors suitable as luminescent materials include, but are not limited to, cerium doped yttrium aluminum garnet ($Y_3Al_5O_{12}:Ce^{3+}$, also referred to as YAG:Ce or Ce doped YAG) or lutetium aluminum garnet (LuAG, $Lu_3Al_5O_{12}$), α-SiAlON:$Eu^{2+}$ (yellow), and $M_2Si_5N_8:Eu^{2+}$ (red) wherein M is at least one element selected from calcium Ca, Sr and Ba. Furthermore, a part of the aluminum may be substituted with gadolinium (Gd) or gallium (Ga), wherein more Gd results in a red shift of the yellow emission. Other suitable materials may include $(Sr_{1-x-y}Ba_xCa_y)_{2-z}Si_{5-a}Al_aN_{8-a}O_a:Eu_z^{2+}$ wherein $0 \leq a < 5$, $0 \leq x \leq 1$, $0 \leq y \leq 1$ and $0 < z \leq 1$, and $(x+y) \leq 1$, such as $Sr_2Si_5N_8:Eu^{2+}$ which emits light in the red range.

Particles of inorganic phosphors may be dispersed in a matrix polymer, such as, for example, Polymethyl methacrylate (PMMA), Polyethylene terephthalate (PET), Polyethylene naphthalate (PEN) or polycarbonate (PC). The inorganic phosphors may also be dispersed in Silicone or other epoxies and/or resins. In other embodiments, an inorganic phosphor forms the basis of a ceramic luminescent layer.

Organic phosphors have a high quantum efficiency and are often transparent, which prevents undesired scattering and increases efficiency. Organic luminescent materials have more advantages. The position and the bandwidth of the luminescence spectrum can be designed with ease to be anywhere in the visible range. As such it is relatively easy to manufacture a light source which emits white light with high efficacy. The white light may be a combination of at least two colors of light, and thus the light source may comprise a single light emitter that emits light of a first color and comprise at least one organic luminescent material that converts a part of the light of the first color into a light of a second color.

The organic phosphor may be a material which comprises a perylene derivative, such as a yellow emitting perylene derivative, or a red/orange emitting perylene derivate. Such perylene derivatives are commercially available under the name Lumogen Yellow F083 or F170, Lumogen Red F305 and Lumogen Orange F240.

There is a nearly unlimited assortment of such organic luminescent materials or dyes. Relevant examples are perylenes (such as dyes known under their trade name Lumogen from the company BASF, Ludwigshafen, Germany: Lumogen F240 Orange, Lumogen F300 Red Lumogen F305 Red, Lumogen F083 Yellow, Lumogen F170 Yellow, Lumogen F850 Green), Yellow 172 from the company Neelikon Food Dyes & Chemical Ltd., Mumbai, India, and dyes such as coumarins (for example Coumarin 6, Coumarin 7, Coumarin 30, Coumarin 153, Basic Yellow 51), napthalimides (for example Solvent Yellow 11, Solvent Yellow 116), Fluorol 7GA, pyridines (for example pyridine 1), pyrromethenes (such as Pyrromethene 546, Pyrromethene 567), uranine, rhodamines (for example Rhodamine 110, Rhodamine B, Rhodamine 6G, Rhodamine 3B, Rhodamine 101, Sulphorhodamine 101, Sulphorhodamine 640, Basic Violet 11, Basic Red 2), cyanines (for example phthalocyanine, DCM), stilbenes (for example Bis-MSB, DPS), available from many traders. Several other dyes, such as acid dyes, basic dyes, direct dyes and dispersion dyes may be used as long as they show a sufficiently high fluorescence quantum yield for the intended use. Hence, one or more of the luminescent moieties may comprise perylene groups. Especially, one or more luminescent moieties are configured to generate red luminescence upon excitation by blue and/or UV light.

Molecules of organic phosphors may be dissolved in a matrix polymer, such as, for example, Polymethyl methacrylate (PMMA), Polyethylene terephthalate (PET), Polyethylene naphthalate (PEN) or polycarbonate (PC). The molecules of organic phosphor may also be dissolved in Silicone or in epoxies or resins.

It is well-known to the skilled person how to manufacture layers of luminescent materials and how to apply them on other layers, such as, for example, the supporting layer.

FIG. 5 schematically shows an embodiment of a luminaire 500, 510. The luminaire 500, 510 comprises at least one color conversion arrangement as disclosed in the context of FIGS. 1a to 1d or FIGS. 4a to 4d, and/or which comprises at least one lighting unit as disclosed in the context of FIG. 2 or FIGS. 3a and 3b.

Summarized, the invention provides a light source, a luminaire and a surgical illumination unit in which two narrow-band light emitters both emit light in a narrow spectral peak having a full-width-half-maximum equal to or smaller than 40 nanometers. Both of the narrow-band light emitters have a different central emission wavelength within a blue color-range, within a green color range or within a red color-range. At least one of the two narrow-band light emitters comprises a luminescent material for generating the narrow spectral peak. The light source is further configured such that a distance between the narrow spectral peaks of the two narrow-band light emitters prevents overlap of the narrow spectral peaks. Due to the individual narrow spectral peaks, a color contrast within one of the color-ranges is significantly enhanced.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A light source, comprising:
   a plurality of narrow-band light emitters, each emitting light in a narrow spectral peak having a full-width-half-maximum equal to or smaller than 40 nanometers and each narrow spectral peak having a central emission wavelength within a blue color-range or within a green color-range or within a red color-range;
   at least one of the narrow-band light emitters comprising a luminescent material for generating the narrow spectral peak thereof; and
   a distance between neighboring ones of the narrow spectral peaks of the narrow-band light emitters at half maximum intensity being configured to prevent overlap of the neighboring ones of the narrow spectral peaks,
   wherein the neighboring ones of the narrow spectral peaks are directly adjacent and the distance is equal to or larger than 40 nanometers and configured to strengthen a contrast perceived between the directly adjacent spectral peaks, and
   wherein a first central emission wavelength of the narrow spectral peaks within the red color-range corresponds to a color of a specific tissue to be operated upon by a surgical instrument, and a second central emission wavelength of the narrow spectral peaks corresponds to a color of the surgical instrument.

2. The light source according to claim 1, wherein the first central emission wavelength lies within a wavelength range between 590 nanometers and 800 nanometers.

3. The light source according to claim 1, wherein the luminescent material comprises any one of the materials from a list comprising: quantum dots, quantum rods or quantum tetrapods, nano-crystals, and rare earth metal complexes with narrow emission characteristics.

4. The light source according to claim 1, wherein the blue color-range or green color-range or red color-range is expanded to an expanded wavelength range between 400 nanometers and 800 nanometers, and wherein the light source is configured to comprise five narrow-band light emitters each of the five narrow-band light emitters emitting light in a narrow spectral peak having a full-width-half-maximum equal to or smaller than 40 nanometers and each of the five narrow-band light emitters having a different central emission wavelength within the expanded wavelength range.

5. The light source according to claim 1, wherein an overall light emission spectrum within the blue color-range, green color-range, red color-range, or within an expanded wavelength range further comprises light emitted in a wide spectral band having an intensity equal to or less than 25% of an average intensity of the narrow spectral peaks.

6. The light source according to claim 1, wherein the luminescent material is arranged:
   on a light exit surface of a light emitting device; and/or
   in a vicinity of the light exit surface of the light emitting device; and/or
   in a remote location from the light exit surface of the light emitting device.

7. The light source according to claim 1, wherein at least one of the narrow-band light emitters is chosen from a list comprising: a Light Emitting Diode, an Organic Light Emitting Diode and a Laser Diode.

8. A luminaire comprising the light source of claim 1.

9. A surgical light source comprising the light source of claim 1.

10. The light source according to claim 3, wherein the central emission wavelength of the narrow spectral peak of the light emitted by the at least one narrowband light emitter comprising the luminescent material is tuned to a predefined wavelength for enhancing a contrast of a predefined visible element.

11. The light source according to claim 4, wherein a sum of the fullwidth-half-maximum value of the narrow spectral peaks within the expanded wavelength range is substantially equal to half the expanded wavelength range.

12. The light source according to claim 6, wherein the luminescent material comprises a mixture of different luminescent materials, at least one of the different luminescent materials being a narrow-band light emitter emitting light at a different central wavelength and having a narrow spectral peak having a full-width-half-maximum equal to or smaller than 40 nanometers.

13. The light source according to claim 6, wherein the light emission spectrum of the light source comprises light emitted by the light emitting device.

* * * * *